United States Patent [19]

Elmquist

[11] 4,302,369

[45] Nov. 24, 1981

[54] ALUMINUM MODIFIED WATER ABSORBENT COMPOSITION

[75] Inventor: Lyle F. Elmquist, St. Paul, Minn.

[73] Assignee: Henkel Corporation, Minneapolis, Minn.

[21] Appl. No.: 138,466

[22] Filed: Apr. 8, 1980

[51] Int. Cl.³ .......................... C08L 3/02; C08L 3/04
[52] U.S. Cl. ...................... 260/17.4 GC; 260/17.4 ST
[58] Field of Search ................. 260/17.4 GC, 17.4 ST

[56] References Cited

U.S. PATENT DOCUMENTS

| | | | |
|---|---|---|---|
| 3,826,767 | 7/1974 | Hoover et al. | 260/17.4 ST |
| 3,935,099 | 1/1976 | Weaver et al. | 210/43 |
| 3,997,484 | 12/1976 | Weaver et al. | 260/17.4 ST |
| 4,043,952 | 8/1977 | Ganslaw et al. | 260/17.4 ST |
| 4,204,983 | 5/1980 | Swarthout et al. | 260/17.4 GC |
| 4,221,684 | 9/1980 | Antholz et al. | 260/17.4 GC |

*Primary Examiner*—John Kight, III
*Assistant Examiner*—N. M. Nutter
*Attorney, Agent, or Firm*—Forrest L. Collins; Patrick J. Span

[57] ABSTRACT

The present invention describes a composition useful for absorbing substantial quantities of water and a preferred process for the manufacture of such compositions.

8 Claims, No Drawings

ALUMINUM MODIFIED WATER ABSORBENT COMPOSITION

BACKGROUND OF THE INVENTION

1. Field of the Invention

This invention relates to methods for entrapment of substantial quantities of aqueous fluids.

2. Description of the Art Practices

It is known that many compositions will absorb aqueous fluids to some degree. Within the last few years, however, it has become possible to develop products which absorb several hundred times their own weight of pure distilled water. When free ions are present in the water, such as from sodium chloride, however, the overall absorbency of the compositions is significantly lessened. This presents some difficulty when the fluid to be absorbed is urine, menstrual discharge, or other bodily fluids such as collect in wounds which have high ionic strength.

Thus, a requirement for the practical application of a water absorbent polymer is that the material retain a high capacity for the absorbence of the fluid, even in the presence of ions such as sodium.

A second problem which is observed in the development of such water absorbent products is that while having a high capacity to absorb the aqueous fluid they do not do so because of the surface wetting phenomena of the particles. That is, under the best conditions, several hundred times the weight of the water absorbent polymer will be absorbed when using deionized water. The problem is, however, that this is done under conditions of ideal mixing. However, when dealing with a bandage, cetamenial tampon, or a diaper, the water absorbent polymer is fixed in its position with relation to the aqueous fluid to be absorbed. Therefore, when surface wetting occurs, it is observed that the first portion of the aqueous fluid to contact the water absorbent polymer is rapidly absorbed on the surface thereof. However, this first portion of the aqueous fluid does, by a mechanism not fully understood, block the remaining flow of the aqueous fluid into the interior of the water absorbent polymer.

It has been proposed in U.S. Pat. No. 4,043,952, issued to Ganslaw, et al, on Aug. 23, 1977 to modify only the surface of a water absorbent polymer to improve the overall absorbence capability of the water absorbent polymer. This method of effecting the surface characteristic is said, by the author of the foregoing reference, to improve the dispersability of the water absorbent polymer. That is, by altering the surface of the polymer with metallic ions, it is stated to be possible to increase the water carrying capacity of the polymer. It is also stated in the Ganslaw, et al. patent that any polyvalent cation may be employed in the surface treating, but with the express requirement that the linkage density at the particle surface must be greater than the linkage density at the particle interior. By greater linkage density at the particle surface, it is meant that the number of ionic linkages on the surface of the polymer molecule are in greater number than in the respective interior portion of the molecule.

While modifying the absorbent characteristics of a polymer may work in some instances, it can not be stated to be a predictable. That is, even though the foregoing reference states that any polyvalent cation may be employed, it has been observed that, with certain water absorbent polymers, the use of certain polyvalent cations renders the water absorbent polymer substantially inactive. That is, not only does the product not wick (absorb rapidly), it loses substantial capability to absorb water when compared to the basic polymer which has not been reacted with the polyvalent cation.

The present invention is particularly concerned with hydrolyzed starch graft copolymers which exhibit substantial capacity to absorb several hundred times their own weight of water with rapid wicking. The development of the original (unmodified) compositions was carried out by the Northern Regional Research Laboratory of the U.S. Department of Agriculture. The basic hydrolyzed starch polyacrylonitrile graft copolymer is produced through free-radical polymerization followed by base hydrolysis.

In the free-radical polymerization process, starch, either gelatinized or ungelatinized, is exposed to a catalyst such as ceric ammonium nitrate which is capable of generating free-radicals in the starch chain. The free-radical generation may also be accomplished through the use of gamma radiation. The overall result is to add polyacrylonitrile chains to the starch free-radicals thus forming the copolymer. In this regard, a description of the processes may be found in U.S. Pat. No. 3,935,099 issued to Weaver, et al. In this reference it is suggested that the ratio of the starch to the polyacrylonitrile should be on a molar basis from about 1:1.5 to 1:9. The variations in the molar ratio of the components of the copolymer are not apparently critical to the practice of the present invention. The resulting copolymer which contains nitrile groups is then hydrolyzed using a strong base such as sodium or potassium hydroxide in the presence of water to convert the nitrile groups to carboxyls and amides. It is observed, in carrying out the hydrolysis step that an extremely strong base is required and materials such as ammonium hydroxide are not suitable for the conversion of the nitrile groups.

The hydrolyzed material may then be dried by any convenient method, such as tumbling or vacuum drying. It is often convenient, prior to drying the absorbent polymer, to wash it with an alcohol to remove any excess ions present, i.e. excess caustic, to substantially increase the absorbency of the composition.

It is noted, however, that the foregoing is accomplished using ideal conditions with respect to dispersability and absorbent capacity. That is, the product, when placed in a diaper or bandage as previously suggested, may well suffer from a lack of absorbency due to the surface wetting phenomenon. It has previously been suggested that such hydrolyzed starch polyacrylonitrile graft copolymers may be modified through treatment with formaldehyde to form a cross-linked product which has increased water absorption capability. The difficulty, of course, involved in this process involves the handling of formaldehyde which, while used in substantial industrial operations, is nonetheless still a hazardous material. Moreover, extreme care must be taken to remove as much unreacted formaldehyde as possible from the copolymer as it is to be used in contact with the human body. Thus, there is a need to obtain a highly water absorbent composition made from a hydrolyzed starch polyacrylonitrile graft copolymer having increased absorbence and wicking without any deleterious side effects.

The present invention has, through treatment of the hydrolyzed starch polyacrylonitrile graft copolymer with aluminum ions, obtained a product having a substantially enhanced degree of wicking and overall improved absorbence.

Through the specification and claims, percentages and ratios are given by weight unless otherwise indicated and temperatures are in degrees Celsius.

SUMMARY OF THE INVENTION

A hydrolyzed starch graft copolymer having in its anionic form carboxyl and amide functionality wherein a substantial portion of the anionic form of the hydrolyzed starch graft copolymer is uniformly reacted to form the aluminum salt.

DETAILED DESCRIPTION OF THE INVENTION

The hydrolyzed starch graft copolymer is formed according to the known methods of preparing such materials and is basically the same as that product marketed under the Henkel Corporation Trademark SGP ® 502S absorbent polymer and SUPER SLURPER TM absorbent polymer. However, in the manufacture of the present invention, prior to isolation of the product, it is treated with a source of aluminum during or following hydrolysis to give the aluminum salt of the anionic form.

Basically, the reaction sequence is to obtain a starch slurry which is then reacted with sufficient quantities of acrylonitrile to form the starch graft copolymer which is then hydrolyzed giving the hydrolyzed copolymer in its anionic form with carboxyl and amide functionality. The proportions of acrylonitrile utilized are such that the overall weight of starch graft copolymer represents approximately from about 25% to about 67% by weight of the starting starch and from about 33% to about 75% by weight of the polymerized acrylonitrile. Wide variations in the properties of the product may be obtained by varying the ratio of the acrylonitrile to the starch. The starting starch material may be cornstarch, potato starch, the grain starches such as wheat, rye or barley, or any material having a glucoside backbone. Most preferably, the starting material is cornstarch.

The grafting of the acrylonitrile onto the starch is accomplished by forming a slurry of the starch and adding the desired quantity of acrylonitrile followed by some step to initiate the grafting process. Conveniently, chemical initiators are used to generate free radicals. The most desired free radical initiators are ceric salts, such as ceric ammonium nitrate. It is believed that initially a starch ceric complex is formed and, thereafter, the ceric ion is reduced to cerous ion. Concomitently, a hydrogen ion is oxidized and a free radical is formed on the starch while the bond between the second and third carbon atoms in the glucose unit is broken. The course of the reaction proceeds through propagation wherein the acrylonitrile is added to the starch molecule and the reaction is continued through transfer of the free radical to the added acrylonitrile group. The reaction conditions are selected such that termination of the reaction does not occur prior to desired weight of acrylonitrile being added to the starch molecule.

It is also possible to generate the free radical through gamma radiation utilizing materials such as cobalt 60, or through the use of high energy electrons from an electron beam source. It is preferred, however, in the present invention to use the ceric salts as the free radical generator. The product so formed contains free nitrile groups added through the polymerization reaction.

At this point, it is necessary to convert the nitrile groups through alkaline hydrolysis to generate the salt of the hydrolyzed starch graft copolymer. This hydrolysis is accomplished using a strong base such as sodium or potassium hydroxide. Weaker bases, such as ammonium hydroxide, do not work effectively to hydrolyze the nitrile group.

The hydrolyzed product will contain both the carboxylate and the amide functional groups. The respective proportion of the carboxylate to the amide is from about 0.1:1 to about 9:0.1; preferably from about 1:1 to about 9:1.

At this point, the processing with the source of aluminum to generate the aluminum salt of the free acid form is discussed. That is, to obtain the benefits of the present invention, the aluminum salt must be formed prior to the drying of the hydrolyzed starch graft copolymer to avoid obtaining a product which is merely surface treated.

The source of aluminum may be added as any of the salts of aluminum, or as aluminum hydroxide. It is first possible to utilize the aluminum source during hydrolysis to from the aluminum salt. However, the basic strength of even aluminum hydroxide is not sufficient to allow a free substitution for the much stronger bases such as sodium or potassium hydroxide which are utilized in the hydrolysis step. However, mixtures of aluminum hydroxide or the aluminum salts with the strong base are possible. Salts of aluminum which may be conveniently employed are aluminum chloride, aluminum acetate or basic aluminum acetate. Of course, it will be recognized that mixtures of the foregoing aluminum salts and/or the hydroxides may be utilized as well in the present invention.

The amount of aluminum ion added should be sufficient in any event to react with the carboxyl groups of the absorbent polymer such that from about 5% to about 95%; preferrably from about 10% to about 75%; and most preferrably from about 15% to about 50% by weight of the total carboxyl groups of hydrolyzed starch graft copolymer are reacted. This may be done by determining the carboxyl content of the anionic form and then calculating the amount of aluminum required to obtain the aluminum salt as described above.

It is essential in the present invention that the linkage density be substantially uniform throughout the hydrolyzed starch graft copolymer. It is, however, possible to obtain a slightly increased benefit in the present invention through surface treating of the previously aluminum modified absorbent polymers. That is, the product of the present invention is obtained and the product thereafter surface treated according to the method shown in U.S. Pat. No. 4,043,952 herein incorporated by reference.

The surface modification of the previously aluminum modified absorbent polymer may be accomplished using any convenient amount of aluminum ion. It is, of course, also possible following the teachings in the foregoing patent to modify the surface of the copolymer utilizing other salts as well. It should be noted, however, that the advantages gained from the surface modification are not as dramatic as the basic benefit in incresed absorbency and wicking obtained from the modification with the aluminum to give a uniform linkage density.

The following are examples of the present invention:

EXAMPLE I

An absorbent polymer is formed according to the present invention from an aqueous dispersion of an acrylonitrile starch graft copolymer containing about 55% adduction of the starch polymer with acrylonitrile. This product is then hydrolyzed with an excess amount of caustic and is then dispersed in an equal amount of deionized water in a blender. Thirty-three parts (dry) of this product are reacted with 8.25 parts of basic aluminum acetate which is sheared into the thick dispersion. The product is isolated by adding 200 parts of methanol to approximately 100 parts of the dispersion in a blender. The mixture of the dispersion and the methanol is then sheared at high speed for approximately one minute to precipitate the polymer which is then poured into a beaker.

The solids are allowed to settle and the supernatant is decanted and 200 parts of fresh methanol is then added. The product is then neutralized over a period of one hour and the solids present are removed by filtration. The neutralization of the solids is accomplished through the addition of hydrochloric acid to neutralize any residual caustic remaining in the product, thereby essentially providing the product at a neutral pH.

The product is dried for a period of about two hours in a forced air oven at approximately 60° C. The solids are passed through a 30 mesh screen and tested for absorbency and wicking properties with the following results: The absorbency of deionized water in grams per gram of product are 369 grams per gram. The wicking time for a 0.1 gram sample of product to fully wet out when dropped onto wet filter paper in contact with a perforated plate floating in deionized water is 30 seconds.

This product is highly satisfactory as it rapidly absorbs several hundred times its weight in water.

EXAMPLE II

Seven hundred parts of a gel containing one hundred parts solids as utilized in Example I are added to a mixer and thereafter 19.3 parts of aluminum chloride hexahydrate are added. Mixing is then commenced and continued for a period of approximately one hour. The product is isolated as in Example I. The same procedure is repeated utilizing at various levels 14.5; 9.7 and zero parts of aluminum chloride hexahydrate. The products are tested as in above with the following results:

TABLE I

| Aluminum Chloride,g | Absorbency,g/g | | |
|---|---|---|---|
| | DI Water | 1% NaCl | Wicking Time |
| 19.3 | 315 | 53 | 30 sec. |
| 14.5 | 338 | 56 | ~3½ min. |
| 9.7 | 463 | 64 | 10 min.+* |
| 0 (Control) | 1421 | 81 | 10 min.+ |

*The test is stopped after a period of 10 minutes and the product is observed to visually determine the degree of wicking and absorbency. The wicking of this sample is substantially greater than that of the control sample shown immediately below.

In the above table the absorbency in grams of the absorbent polymer (Modified or unmodified) is shown. The figure 1% sodium chloride indicates a 1% by weight water solution of sodium chloride and its respective absorbency by the polymer. The wicking time is the time required for 0.1 gram of the product to fully wet out when dropped onto wet filter paper in contact with a perforated plate floating in deionized water. The figures above show that the treatment of product with aluminum slightly reduces the overall absorbency of the product directly proportional to the increased aluminum level. However, the wicking time is substantially improved through obtaining a product which has been modified throughout with the aluminum ions.

EXAMPLE III

A slurry containing approximately 100 parts of solids, 714 parts overall of acrylonitrile starch graft copolymer is added to a mixer. 76.5 parts sodium hydroxide and 9.1 parts of aluminum hydroxide are then dissolved in 86 parts of deionized water. This second mixture is then added to the mixer with stirring. The combined product is then heated with steam at above 85° C. for approximately one and one-half hours followed by cooling to room temperature. The hydrolyzed product is isolated as in Example I. The same procedure is also repeated utilizing 6.0 parts of aluminum hydroxide and the product is otherwise treated as shown above.

The products were tested as previously described and results are shown in Table II below:

TABLE II

| Aluminum Hydroxide, g | Absorbency, g/g | | |
|---|---|---|---|
| | DI Water | 1% NaCl | Wicking Time |
| 9.1 | 245 | 44 | 8 sec. |
| 6.0 | 321 | 47 | 23 sec. |

What is claimed is:

1. A hydrolyzed starch graft copolymer having in its anionic form carboxyl and amide functionality wherein a substantial portion of the anionic form of the hydroxyzed starch graft copolymer is uniformly reacted to form the aluminum salt said aluminum salt being formed prior to the drying of the hydrolyzed starch graft copolymer wherein from about 5 percent to about 95 percent by weight of the free carboxyl groups present are neutralized with aluminum.

2. The hydrolyzed starch graft copolymer of claim 1 wherein from about 10% to about 75% by weight of free carboxyl groups are neutralized with aluminum.

3. A process for preparing a compound according to claim 1 wherein the aluminum salt is formed during alkaline hydrolysis of the acrylonitrile starch graft copolymer.

4. The process of claim 3 wherein the basic form of aluminum is employed during hydrolysis.

5. The process of claim 3 wherein the basic form of aluminum is aluminum hydroxide.

6. The process of claim 3 wherein the excess base is washed out of the starch graft copolymer with an alcohol.

7. The process of claim 3 wherein the aluminum salt is formed subsequent to hydrolysis.

8. A process according to claim 3 wherein the hydrolyzed starch graft copolymer is surface treated in a subsequent step to form a product having a linkage density at the particle surface greater than the linkage density in the particle interior.

* * * * *